US00PP19787P2

(12) United States Plant Patent
Danziger

(10) Patent No.: US PP19,787 P2
(45) Date of Patent: Mar. 3, 2009

(54) ***JAMESBRITTENIA* PLANT NAMED 'DANBRIT7'**

(50) Latin Name: *Jamesbrittenia hybrida*
Varietal Denomination: Danbrit7

(76) Inventor: Gabriel Danziger, PO Box 24, Moshav Mishmar Hashiva, Beit Dagan (IL), 50297

( * ) Notice: Subject to any disclaimer, the term of this patent is extended or adjusted under 35 U.S.C. 154(b) by 0 days.

(21) Appl. No.: 12/008,423

(22) Filed: Jan. 11, 2008

(51) Int. Cl.
*A01H 5/00* (2006.01)

(52) U.S. Cl. ..... Plt./485
(58) Field of Classification Search ..... Plt./485
See application file for complete search history.

*Primary Examiner*—Annette H Para
*Assistant Examiner*—S. B. McCormick-Ewoldt

(57) ABSTRACT

A new and distinct *Jamesbrittenia* cultivar named 'DANBRIT7' is disclosed, characterized by having large, pink flowers, with a distinctive darker center halo, a compact, mounded and upright plant habit and continuous flowering. The new variety is a *Jamesbrittenia,* normally produced as an outdoor garden or container plant.

2 Drawing Sheets

Latin name of the genus and species: *Jamesbrittenia hybrida.*
Variety denomination: 'DANBRIT7'.

BACKGROUND OF THE INVENTION

The new cultivar is a product of a planned breeding program, conducted by the inventor, Gabriel Danziger in Moshav Mishmar Hashiva, Israel. The objective of the breeding program was to produce plants of *Jamesbrittenia hybrida* with compact habits and large pink flowers. The seed parent is the unpatented, proprietary seedling variety referred to as *Jamesbrittenia hybrida* 'cv.4-323'. The pollen parent is unknown as the new variety 'DANBRIT7' is a result of open pollination, in which the pollen parent cannot be identified. The new variety was discovered in October 2005 by the inventor in a group of seedlings resulting from that crossing, in Moshav Mishmar Hashiva, Israel.

Asexual reproduction of the new cultivar 'DANBRIT7' by vegetative cuttings was first performed at a commercial greenhouse in Moshav Mishmar Hashiva, Israel in November 2005 and has shown that the unique features of this cultivar are stable and reproduced true to type on successive generations.

SUMMARY OF THE INVENTION

The cultivar 'DANBRIT7' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DANBRIT7' These characteristics in combination distinguish 'DANBRIT7' as a new and distinct *Jamesbrittenia* cultivar:

1. Compact plant habit.
2. Very large flowers.
3. Unique flower color of light pink with a large yellow center surrounded by a darker halo.

4. Very upright habit.
5. Small foliage.

COMPARISON TO PARENT VARIETY

Plants of the new cultivar 'DANBRIT7' are similar to plants of the seed parent, *Jamesbrittenia hybrida* 'cv.4-323' in most horticultural characteristics, however, plants of the new cultivar 'DANBRIT7' produce flowers of a darker pink, with a larger yellow center. Additionally, 'DANBRIT7' plants are more upright than the female parent.

COMMERCIAL COMPARISON

Plants of the new cultivar 'DANBRIT7' can be compared to plants of the commercial variety *Jamesbrittenia hybrida* 'DANBRIT2', an unpatented, variety in the United States, in most horticultural characteristics, however, plants of the new cultivar have larger flowers of a lighter pink color, with a darker halo. Additionally, the new variety has a more upright plant habit and smaller leaves then 'DANBRIT2.'

BRIEF DESCRIPTION OF THE PHOTOGRAPH

Figure 1:
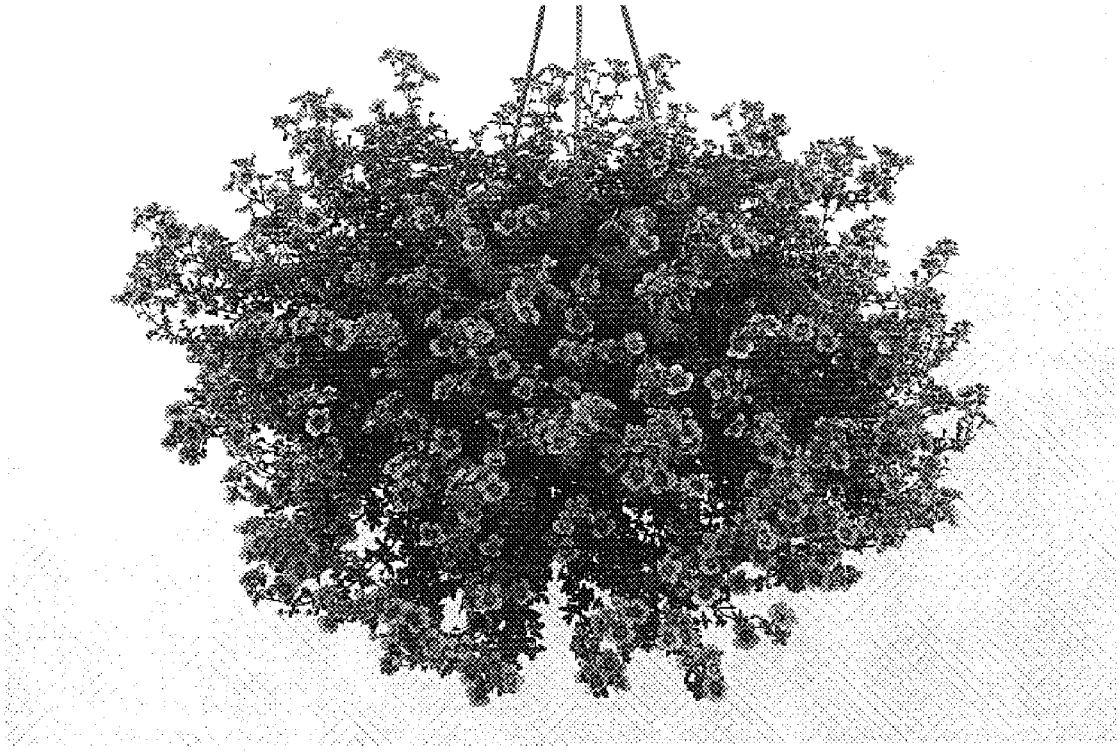

The accompanying photograph in FIG. 1 illustrates in full color a typical plant of 'DANBRIT7' grown in a greenhouse, in a 13 cm basket. Age of the plant photographed is approximately 3 months from a rooted cutting.

Figure 2:
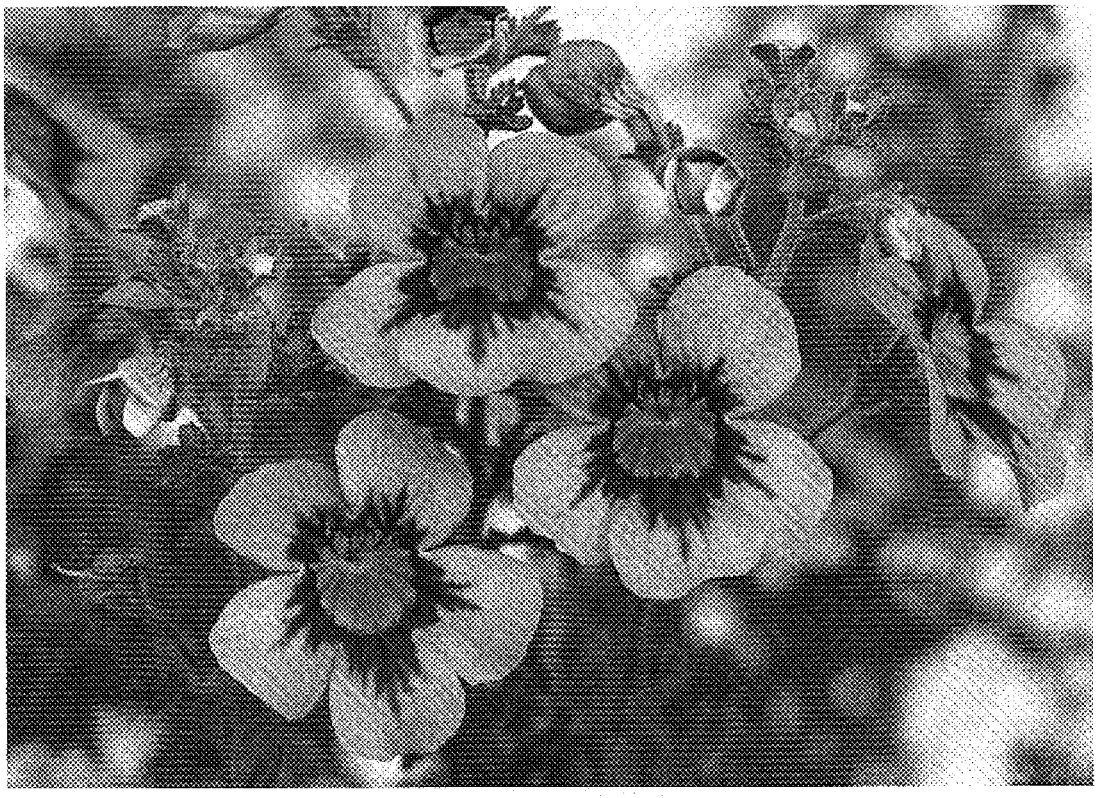

FIG. 2 illustrates in full color a close up of a typical bloom of 'DANBRIT7.'

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'DANBRIT7' plants grown in a greenhouse in Moshav Mishmar Hashiva, Israel. The growing temperature ranged from 18° C. to 24° C. The greenhouse is subject to partial shade. General light conditions are bright, normal sunlight, with some shade during the brightest part of the day. Measurements and numerical values represent averages of typical plant types.

Botanical classification: *Jamesbrittenia hybrida* cultivar 'DANBRIT7.'

PROPAGATION

Time to initiate roots: About 7 to 10 days at approximately 18° C.
Root description: Fine, densely fibrous.
Time to produce a rooted cutting: About 14 to 18 days at 18° C.

PLANT

Growth habit: Mounding annual.
Pot size of plant described: 13 cm.
Age of plant described: Approximately 90 days from a rooted cutting.
Height:
*To top of foliage.*—Approximately 22 cm.
Plant spread: Approximately 50 cm.
Growth rate: Moderate.
Branching characteristics: Well-branched, all branches occurring at ground level, there is no central or main branch.
Length of primary lateral branches: Approximately 22 cm.
Diameter of lateral branches: Approximately 0.2 cm.
Quantity of primary lateral branches: About 10.
Characteristics of primary lateral branches:
*Form.*—Cylindrical.
*Color.*—Near RHS Yellow-Green 146 C.
*Texture.*—Slightly pubescent
*Strength.*—Strong.
Internode length: Approximately 1 cm.

FOLIAGE

Leaf:
*Arrangement.*—Opposite.
*Quantity.*—Approximately 40 per branch.
*Average length.*—Approximately 2 cm.
*Average width.*—Approximately 1 cm.
*Shape of blade.*—Ovate.
*Apex.*—Obtuse.
*Base.*—Acute.
*Margin.*—Serrate.
*Texture of top surface.*—Velvety.
*Pubescence.*—Slightly pubescent.
*Foliage fragrance.*—Lemony.
*Color.*—Young foliage upper side: Near RHS Green 137C. Young foliage under side: Near RHS Green 137C. Mature foliage upper side: Near RHS Green 137B. Mature foliage under side: Near RHS Green 137B.
*Venation.*—Type: Pinnate. Venation color upper side: Near RHS Green 137B. Venation color under side: Near RHS Green 137C.
*Petiole.*—Length: Approximately 0.4 cm. Diameter: Approximately 0.1 cm. Color: Near RHS Green 137C. Texture: Velvety.

FLOWER

Natural flowering season: Freely flowering under outdoors growing conditions with substantially continuous blooming from spring through autumn. Year round in greenhouse environment, or under warm conditions and high sunlight. Flowering begins approximately 6 weeks after planting a rooted cutting.
Inflorescence and flower type and habit: Individual flowers are typical scrophulariaceae shape, 2-lipped, 5-petaled solitary flowers, fused at base, occurring in the leaf axis, on a terminal raceme.
Rate of flower opening: Approximately 4 days from bud to fully opened flower.
Flower longevity on plant: Individual flowers last approximately 7 days on the plant.
Flower form: Salvaform.
Flower size:
*Diameter.*—Approximately 2 cm.
*Length.*—Approximately 1 cm.
*Corolla tube diameter.*—Approximately 0.2 cm.
Corolla/petals:
*Arrangement.*—5 rounded and gameopetalous petals.
*Length.*—About 0.7 cm.
*Diameter.*—About 0.7 cm.
*Quantity.*—5.
*Texture.*—Velvety.
*Apex.*—Obtuse.
*Base.*—Fused.
*Margin.*—Entire.
Color:
*When opening.*—Upper surface: Near RHS Red-Purple N57D. Lower surface: Near RHS Red-Purple N587D.
*Fully opened.*—Upper surface: Near RHS Red-Purple N57D; darker halo, Red 53C Yellow center RHS 24A. Lower surface: Near RHS Red-Purple N58D.
Corolla tube color: Near RHS yellow-Green 145B.
Bud:
*Shape.*—Slightly flattened sphere.
*Length.*—Approximately 0.7 cm.
*Diameter.*—Approximately 0.4 cm.
*Color.*—Near RHS Purple-Red N57C.
Calyx/sepals:
*Quantity per flower.*—5, fused at base.
*Shape.*—Oblong.
*Length.*—Approximately 0.4 cm.
*Width.*—Approximately 0.1 cm.
*Apex.*—Mucronulate.
*Base.*—Fused.
*Margin.*—Entire.
*Texture.*—Velvety.
*Color.*—Upper Surface: Near RHS Yellow-Green 146B. Lower Surface: Near RHS Yellow-Green 146B.
Peduncle: None.
Pedicel:
*Length.*—Approximately 1 cm.
*Diameter.*—Approximately 0.1 cm.
*Color.*—Near RHS Green 137C.
*Orientation.*—Slanted upward at an angle of about 45°.
Fragrance: Lemony.

REPRODUCTIVE ORGANS

Stamens:

*Number.*—4.

*Filament length.*—Approximately 0.5 cm.

*Filament color.*—Near RHS Yellow-Green 154A.

Anthers:

*Shape.*—Cylindrical.

*Length.*—Approximately 0.1 cm.

*Color.*—Near RHS Yellow-Orange 17B.

*Pollen.*—Color: Near RHS Yellow-Orange 17B. Quantity: Scarce.

Pistil:

*Number.*—1.

*Length.*—Approximately 0.7 cm.

*Width.*—Approximately 0.1 cm.

*Style.*—Length: Approximately 0.5 cm. Color: Near RHS Green-yellow 1C.

*Stigma.*—Shape: Round. Color: Near RHS Green 141B.

*Ovary.*—Position: Superior. Shape. Ellipsoid. Color: Near RHS Green 143C. Size. About 0.2 cm.

OTHER CHARACTERISTICS

Seeds and fruits: Seeds are dark brown, rounded, approximately 0.05 cm in diameter.

Disease/pest resistance: The new variety shows good resistance to pathogens and pests common to *Jamesbrittenia.*

Temperature tolerance: The new variety tolerates temperatures between 5 to 35° C.

What is claimed is:

1. A new and distinct cultivar of *Jamesbrittenia* plant named 'DANBRIT7' as herein illustrated and described.

* * * * *